US005462856A

United States Patent [19]
Lerner et al.

[11] Patent Number: 5,462,856
[45] Date of Patent: Oct. 31, 1995

[54] METHODS FOR IDENTIFYING CHEMICALS THAT ACT AS AGONISTS OR ANTAGONISTS FOR RECEPTORS AND OTHER PROTEINS INVOLVED IN SIGNAL TRANSDUCTION VIA PATHWAYS THAT UTILIZE G-PROTEINS

[75] Inventors: Michael R. Lerner, Hamden, Conn.; Ethan A. Lerner, Brookline, Mass.

[73] Assignee: Bunsen Rush laboratories, Inc., Newton, Mass.

[21] Appl. No.: 732,476

[22] Filed: Jul. 16, 1991

Related U.S. Application Data

[63] Continuation-in-part of Ser. No. 555,724, Jul. 19, 1990.
[51] Int. Cl.$^6$ ............................. C12N 15/12; C12N 5/10; G01N 33/566
[52] U.S. Cl. ...................... 435/7.21; 435/7.2; 435/69.1; 435/172.1; 435/240.1; 935/59; 935/70
[58] Field of Search ............................. 435/4, 7.2, 69.1, 435/172.1, 240.1, 7.21; 935/59, 70

OTHER PUBLICATIONS

Etkins et al., Development 99:15–23 (1987).
Expression of a Human cDNA Encoding the $\beta_2$–Adrenergic Receptor in Chinese Hamster Fibroblasts (CHW): Functionality and Regulation of the Expressed Receptors, Michael Bouvier pp. 133–139, Molecular Pharmacology 33, 133–139 et al (1987).
Modecular Characterization of a Functional cDNA Encloding the Serotonin 1c Receptor, David Julius et al Science vol. 241 pp. 558–564, (1988).
Message Transmission: Receptor Controlled Adenylate Cyclase System, Michael Schramm et al, Science, vol. 225, pp. 1350–1356, (1984).
Proc. Natl. Acad. Sci. USA. Vol. 72, No. 2, (1975), Sharma et al., "Morphine receptors as regulators of adenylate cyclase activity," pp. 590–594.
Science, vol. 241, (1988), Julius et al., "Molecular characterization of a functional cDNA encloding the serotonin 1c receptor," pp. 558–564.
J. Biological Chemistry, vol. 262, No. 32, (1987), Kobilka et al., "Functional activity and regulation of human $B_2$–adrenergic receptors expressed in Zenopus oocytes," pp. 15796–15802.
Wardem. D. et al. (1968), J. Gen. Virol., 3: 371–377, "The Infectivity of Polyoma Virus DNA for Mouse Enbryo Cells in the Presence of Diethylaminoethyl–dextran".
Felgner, P. L. et al. (1987), Proc. Natl. Acad. Sci., 84:7413–7417, "Lipofection: A highly efficient, lipid–mediated DNA–transfection procedure".
Boggs, S. S. et al. (1986), Exp. Hematol., 14:988–994, "Efficient Transformation and Frequent Single–site, Single–copy Insertion of DNA Can Be Obtained in Mouse Erythroleukemia Cells Transformed by Electroporation".
Pressman, B. C. (1976), Ann. Rev. Biochem., 45: 501–531.
Jakobs (1979), Molecular and Cellular Endocrinology, 16: 147–156, "Inhibition of Adenylate Cyclase by Hormones and Neurotransmitters".

Lefkowitz (1991), Nature, 351: 353–354, "Variations on a theme".
Kobilka, B. K. et al. (1987), Proc Natl Acad Sci USA 84: 46–50, "cDNA for the human $\beta_2$–adrenergic receptor: A protein with multiple membrane–spanning domains and encoded by a gene whose chromosomal location is shared with that of the receptor for platelet–derived growth factor".
Kobilka, B. K. et al. 91987), Science 238: 650–656, "Cloning, Sequencing, and Expression of the Gene Coding for the Human Platelet $\alpha_2$–Adrenergic Receptor".
Bunzow, J. R. et al. (1988), Nature 336: 783–787, "Cloning and expression of a rat $D_2$ dopamine receptor cDNA".
Simon, M. I. et al. (1991), Science 252: 802–808, "Diversity of G Proteins in Signal Transduction".
Negishi et al. (1988), General and Comparative Endocrinology, 70: 127–132, "A Sensitive Bioassay for Melanotropic Hormones Using Isolated Medaka Melanophores".
Messenger and Warner (1977), Br. J. Pharmac. 61: 607–614, "The Action of Melatonin on Single Amphibian Pigment Cells in Tissue Culture".
Mori and Lerner (1966), Endocrinology, 67: 443–450 (1960) "A Microscopic Bioassay for Melatonin".
Moller and Lerner (1966), Acta Endocrinologica, 51: 149–160, "Melanocyte Simulating Hormone Inhibition by Acetycholine and Noradrenaline in the Frog Skin Bioassay".
Carter and Shuster (1978), J. Inv. Dermatology, 71: 229–232, "A Sensitive New In Vitro Bioassay for Melanocyte–stimulating Activity Using the Skin of Anolis carolinensis".
Lerner et al. (1988), P.N.A.S. USA 85: 261–264, "Olfaction by melanophores: What does it mean?".
Elwing, C. H. et al. (1990), Biosensors & Bioelectronics, 5: 449–459, "Fish Scales as Biosensors for Catecholamines".
Steiner et al. (1972), J. Biol. Chem., 247: 1106–1113, "Radioimmunoassay for Cyclic Nucleotides".

(List continued on next page.)

Primary Examiner—Michael P. Woodward
Attorney, Agent, or Firm—Wolf, Greenfield & Sacks

[57] ABSTRACT

A method for identifying a chemical that acts as an agonist for a G-protein coupled cell surface (GPC) receptor. The method comprises introducing to test cells of a pigment cell line capable of dispersing or aggregating their pigment in response to a specific stimulus and expressing an exogenous clone coding for the GPC receptor, a stimulant that sets an initial state of pigment disposition wherein the pigment is aggregated within the test cells if activation of the exogenous GPC receptor induces pigment dispersion, or introducing a stimulant that sets an initial state of pigment disposition wherein the pigment is dispersed within the test cells if activation of the exogenous GPC receptor induces pigment aggregation; contacting the test cells set in an initial state of pigment disposition with the test chemical; and determining whether the pigment disposition in the test cells treated with the chemical is changed from the initial state of pigment disposition, wherein a change in pigment disposition observed in the test cells expressing the exogenous GPC receptor indicates that the chemical is an agonist for the exogenous GPC receptor.

14 Claims, 10 Drawing Sheets

OTHER PUBLICATIONS

Salomon et al. (1974), *Analytical Biiochemistry* 58: 541–548, "A Highly Sensitive Adenylate Cyclase Assay".

*Pigment Cell 1985*, ed. Bagnara et al. University of Tokyo Press, pp. 219–227, Noel, "Chromatophores Direct Photoreactivity".

Ide (1974) *Developmental Biology* 41, 380–384, Brief Notes.

Wakelam, M. J. O. et al. (1986), *Nature*, 323: 68–71, "Activation of two signal-transduction systems in hepatocytes by glucagon".

Daniolos, A. et al. (1990), *Pigment Cell Research*, 3: 38–43, "Action of Light on Frog Pigment Cells in Culture".

Lerner and Case (1959), *Investigative Dermatology*, 32: 211–221, "Pigment Cell Regulatory Factors".

Butman, B. T. et al. (1979), *J. Exp. Zool.*, 208: 17–34, "Hormone-induced Pigment Translocations in Amphibian Dermal Iridophores, In Vitro: Changes in Cell Shape".

Hogben and Slome (1931), *Proc. Royal Soc. B.*, 108: 10–53, "The Pigmentary Effector System. VI. The Dual Character of Endocrine Co-ordination in Amphibian Colour Change".

Rozdzial and Haimo (1986), *Cell*, 47: 1061–1070, "Bidirectional Pigment Granule Movements of Melanophores Are Regulated by Protein Phosphorylation and Dephosphorylation".

Lynch et al. (1986), *J. Biol. Chem.*, 261: 4212–4216, "Regulation of Pigment Organelle Translocation".

Stryer, L. (1986), *Ann. Rev. Neurosci.*, 9: 87–115, "Cyclic GMP Cascade of Vision".

Hall, C. V. et al. (1983), *J. Mol. Appl. Genet.*, 2: 101–109, "Expression and Regulation of *Escherichia coli* lacZ Gene Fusions in Mammalian Cells".

Harland, R. et al. (1988), *Development*, 102: 837–852, "Stability of RNA in developing Xenopus embryos and identification of a destabilizing sequence in TFIIIA messenger RNA".

Gorman, C. M. et al. (1982), *Proc. natl. Acad. Sci.* 22: 6777–6781, "The *Rous sarcoma* virus long terminal repeat is a strong promoter when introduced into a variety of eukaryotic cells by DNA-mediated transfection".

Spaete, R. R. et al. (1985), *Journal of Virology*, 56: 135–143, "Regulation of Cytomegalovirus Gene Expression: α and β Promoters Are trans Activated by Viral Functions in Permissive Human Fibroblasts".

Sambrook, J. et al. 91989), *Molecular Cloning*, Cold Spring Harbor Laboratory Press 2nd ed. 1610–1612.

McCutchan, J. H. et al. (1968), *J. Natl. Cancer Inst.*, 41: 351–357, "Enhancement of the Infectivity of Simian Virus 40 Deoxyribonucleic Acid With Diethylaminoethyl–Dextran".

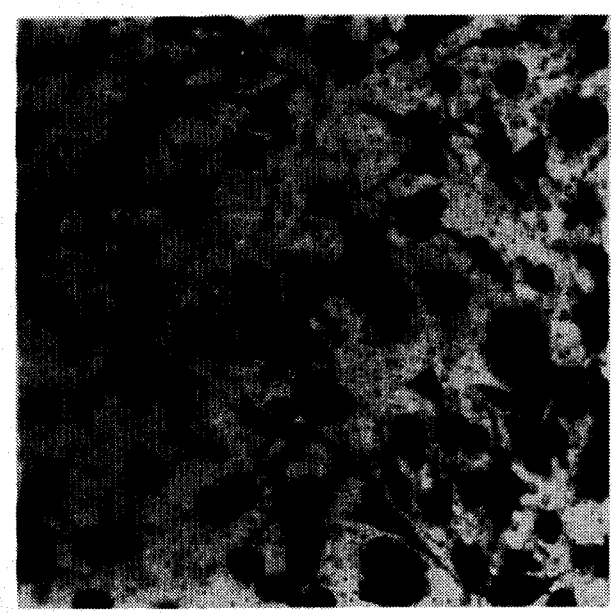
FIG. 7
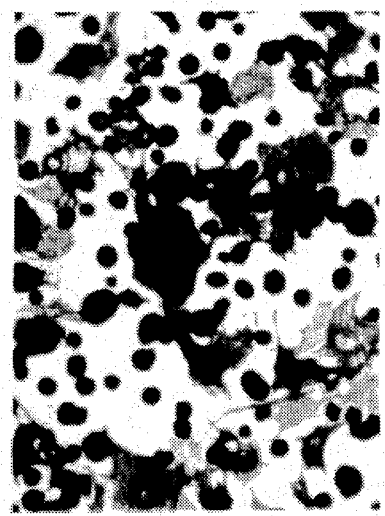 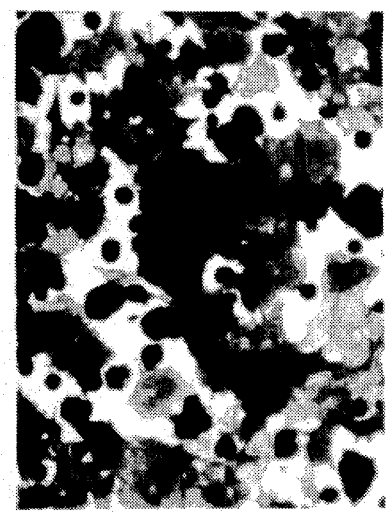 
FIG. 8A    FIG. 8B    FIG. 8C

METHODS FOR IDENTIFYING CHEMICALS THAT ACT AS AGONISTS OR ANTAGONISTS FOR RECEPTORS AND OTHER PROTEINS INVOLVED IN SIGNAL TRANSDUCTION VIA PATHWAYS THAT UTILIZE G-PROTEINS

CROSS-REFERENCE TO RELATED APPLICATION

This application is a continuation-in-part of application Ser. No. 07/555,724, filed Jul. 19, 1990.

BACKGROUND OF THE INVENTION

1. Field of the Invention

The present invention relates to methods for identifying chemicals that act as agonists or antagonists for proteins participating in signal transduction pathways that utilize heterotrimeric guanine nucleotide-binding proteins (G-proteins) and/or second messengers, e.g., cyclic adenosine monophosphate (cAMP) and to a method for identifying nucleic acid clones coding for G-protein coupled cell surface receptors (GPC receptors) that act via signal transduction pathways that utilize G-proteins and/or second messengers, e.g., cAMP.

2. Background Information

All publications referred to herein are incorporated by reference.

It is well established that many medically significant biological processes are mediated by proteins participating in signal transduction pathways that involve G-proteins and/or second messengers, e.g., cAMP (Lefkowitz (1991) *Nature*, 351: 353–354). Herein these proteins are referred to as proteins participating in pathways with G-proteins or PPG proteins. Some examples of these proteins include the GPC receptors such as those for adrenergic agents and dopamine (Kobilka B. K., Dixon, R. A., Frielle, T., et al. (1987) *Proc Natl Acad Sci U S A* 84: 46–50; Kobilka, B. K., Matsui, H., Kobilka, T. S., et al. (1987) *Science* 238: 650–656; Bunzow, J. R., Van Tol, H. H. M., Grandy, D. K., Albert, P., et al. (1988) *Nature* 336:783–787), G-proteins themselves, effector proteins, e.g., phospholipase C, adenyl cyclase, and phosphodiesterase, and actuator proteins, e.g., protein kinase A and protein kinase C (Simon, M. I.; Strathmann, M. P.; Gautam, N., (1991) *Science* 252: 802–8).

Bioassays for chemicals that activate a few GPC receptors that are endogenous in pigment cells are described in Negishi et al. (1988), *General and Comparative Endocrinology*, 70: 127–132; Messenger and Warner (1977) *Br. J. Pharmacology* 61:607–614; Mori and Lerner, (1960) *Endocrinology* 67: 443–450; Moller and Lerner (1966) *Acta Endocrinologica*, 51: 149–160; Carter and Shuster (1978) *J. Inv. Dermatology*, 71:229–232; Lerner et al. (1988), *P.N.A.S. USA* 85: 261–264; and C. H. Elwing et al. (1990), *Biosensors & Bioelectronics*, 5: 449–459.

In all of the methods described in the publications listed above, there are the following six major differences between them and the applicants' methods:

(1) The applicants' methods are based on pigment cells that can be grown in continuous long term culture whereas none of the bioassays described in the above publications makes use of pigment cells that continue to divide in culture. The advantage of the applicants' method is that it allows for the straightforward generation of an unlimited number of cells to be used for assays. Without this ability, large scale drug screens are not possible.

(2) Only the applicants' methods allow for a continuous source of pigment cells generated from existing ones without the need to collect fresh cells from animals.

(3) Only the applicants' methods utilize pigment cells that can be grown to high density in tissue culture vessels. This is important for the ability to screen large numbers of drugs and it is important for the ability to being able to obtain reliable results using standard microtiter plate readers.

(4) The applicants' methods can be used to screen for drugs which affect the endogenous serotonin receptor on pigment cells which causes pigment dispersion. In contrast thereto, in the publications listed above, serotonin is stated to cause pigment aggregation, e.g., Messenger and Warner (1977) *Br. J. Pharmacology* 61:607–614.

(5) The applicants' methods utilize recombinant DNA technology so that the pigment dells can serve as the basis of drug assays for receptors and other proteins that are not naturally expressed by pigment cells. The methods described in the above publications, however, are limited to receptors that are endogenous to pigment cells.

(6) In contrast to the above described publications, only the applicants' methods can be used to clone GPC receptors because the applicants' methods make use of continuous cultures of pigment cells and recombinant DNA technology.

Currently there is a major limitation in finding new and better drugs for GPC receptors, namely, no initial screen exists for testing the abilities of chemicals to affect GPC receptors that is simple, rapid and general. For example, consider assays for evaluating GPC receptors that work via Gs or Gi to raise or lower intercellular cAMP. Radioimmunoassay (RIA) for cAMP accumulation is both expensive, slow and a single technician would be hardpressed to screen more than 20 chemicals in triplicate in a single day (Steiner et al. (1972) *J. Biol. Chem.*, 247: 1106–1113). Meanwhile, the current adenylate cyclase activation assay is faster than the RIA, and a single individual can process up to 150 samples in a day (Salomon et al. (1974) *Analytical Biochemistry* 58: 541–548). However, the current adenylate cyclase activation assay requires several steps and is therefore cumbersome. Also, both procedures involve substantial use of radioactive materials, for example, either $^{32}P$ or $^{125}I$.

Definitions

A "chemical" is defined to include any drug, compound or molecule.

A "G-protein coupled cell surface receptor" (GPC receptor) is defined to be any cell surface transmembrane protein, that when activated by a chemical, in turn activates a heterotrimeric guanine nucleotide-binding protein (G-protein).

A "protein participating in a signal transduction pathway that involves a G-protein and/or a second messenger (PPG protein)" is defined as any protein involved in the pathway including GPC receptors, G-proteins, effector proteins and actuator proteins.

An "effector protein" is defined as any protein which is activated or inactivated by an α subunit of a G-protein. Some examples of effector proteins include adenyl cyclase, phospholipase C and phospholipase A2. Phosphodiesterase is also considered an effector protein.

A "second messenger" is defined as an intermediate compound whose concentration, either intercellularly or within the surrounding cell membrane, is raised or lowered as a consequence of the activity of an effector protein. Some examples of second messengers include cyclic adenosine monophosphate (cAMP), phosphotidyl inositols (PI), such as inositol triphosphate (IP3), diacylglycerol (DAG), calcium (Ca++) and arachidonic acid derivatives.

An "actuator protein" is defined as a protein whose state of activation is modified as a result of binding a second messenger. Some examples of effector proteins include protein kinase A and protein kinase C.

A schematic example that provides a summary of the above definitions by example of one pathway that utilizes G-proteins and the second messenger cAMP is given in FIG. 1.

"Pigment cells" mean any pigment-containing cells that meet the following conditions: (1) They are derived from any animal whose pigment cells are capable of aggregating or dispersing their pigment in response to a specific stimulus, e.g., contact with melanocyte stimulating hormone, melatonin, light, etc, (2) They can be indefinitely propagated in vitro so that unlimited quantities of cells can be obtained. (3) Pigment cells ("test cells") for use in the present invention include the following non-limiting examples of chromatophores: melanophores or melanocytes, xanthophores, erythrophores, leukophores and iridophores. The pigment cells are taken from animals lower on the evolutionary tree than humans and birds. Non-limiting examples of "lower animals" from which pigment cells can be taken for utilization in the present invention include the following: Reptilia, e.g., Anolis sp; Amphibia, e.g., *Xenopus laevis;* Pisces, e.g., *Zacco temmincki;* Crustacia, e.g., *Uca pugilator;* Echinodermata, e.g., *Diadema antillarum* and Cinidaria, e.g., *Nanomsa cara*. Particularly preferred pigment cells for use in the present invention are cultured melanophores from the from *Xenopus laevis* (Pigment Cell 1985), ed. Bagnara et al., University of Tokyo Press, pages 219–227) and Lerner et al. (1988) *P.N.A.S. USA*, 85: 261–264.

SUMMARY OF THE INVENTION

One object of the present invention is to develop rapid and sensitive bioassays for evaluating new agonists and antagonists for PPG proteins and in particular for GPC receptors.

Another object of the present invention is to develop a strategy for cloning DNAs coding for GPC receptors.

Another object of the present invention is to provide kits for carrying out the bioassay methods for evaluating new agonists and antagonists for PPG proteins and in particular for GPC receptors.

These objects and other objects, aims and advantages are satisfied by the present invention.

According to the present invention, a method is provided for identifying a chemical, e.g., a drug, that acts as an agonist for an exogenous GPC receptor. The method comprises introducing to test cells of a pigment cell line capable of dispersing or aggregating their pigment in response to a specific stimulus and expressing an exogenous clone coding for the GPC receptor, a stimulant, e.g., a chemical or light, that sets an initial state of pigment disposition wherein the pigment is aggregated within the test cells if activation of the exogenous GPC receptor induces pigment dispersion, or introducing a stimulant, e.g., a chemical or light that sets an initial state of pigment disposition wherein the pigment is dispersed within the test cells if activation of the exogenous GPC receptor induces pigment aggregation; contacting the test cells set in an initial state of pigment disposition with the chemical; and determining whether the pigment disposition in the test cells treated with the chemical is changed from the initial state of pigment disposition. A control operation can also be performed. The control utilizes the same procedure as described above, except that pigment cells not expressing the exogenous GPC receptor are employed. When a change in pigment disposition is observed in the test cells expressing the exogenous GPC receptor, but no change in pigment disposition is observed in the control cells not expressing the exogenous GPC receptor, the chemical is an agonist for the exogenous GPC receptor.

According to the present invention, a method is provided for identifying a chemical, e.g., a drug, that acts as an agonist for an exogenous PPG protein. The method comprises introducing to test cells of a pigment cell line capable of dispersing or aggregating their pigment in response to a specific stimulus and expressing an exogenous clone coding for the PPG protein, a stimulant, e.g., a chemical or light, that sets an initial state of pigment disposition wherein the pigment is aggregated within the test cells if activation of the exogenous PPG protein induces pigment dispersion, or introducing a stimulant, e.g., a chemical or light, that sets an initial state of pigment disposition wherein the pigment is dispersed within the test cells if activation of the exogenous PPG protein induces pigment aggregation; contacting the test cells set in an initial state of pigment disposition with the chemical; and determining whether the pigment disposition in the test cells treated with the chemical is changed from the initial state of pigment disposition. A control operation may also be performed. The control utilizes the same procedure as set forth above, except that pigment cells not expressing the exogenous PPG protein, are employed. When a change in pigment disposition is observed in the test cells expressing the exogenous PPG protein but no change in pigment disposition is observed in the control cells not expressing the exogenous PPG protein, the chemical is an agonist for the exogenous PPG protein.

The present invention also concerns a method for identifying a chemical that acts as an antagonist for an exogenous GPC receptor. The method comprises introducing to test cells of a pigment cell line capable of dispersing or aggregating their pigment in response to a specific stimulus and expressing an exogenous clone coding for the GPC receptor, a first stimulant, e.g., a chemical or light, that sets an initial state of pigment disposition wherein the pigment is aggregated within the test cells if activation of the exogenous GPC receptor induces pigment dispersion, or introducing a first stimulant, e.g., a chemical or light, that sets an initial state of pigment disposition wherein the pigment is dispersed within the test cells if activation of the exogenous GPC receptor induces pigment aggregation; contacting the test cells set in an initial state of pigment disposition with the chemical to be identified; observing the cells to determine that their state of pigment disposition remains unchanged; adding to the test cells contacted with the chemical to be identified, a second stimulant, that induces pigment dispersion by activating the exogenous GPC receptor if activation of the exogenous GPC receptor induces pigment dispersion, or adding a second stimulant that induces pigment aggregation by activating the exogenous GPC receptor if activation of the exogenous GPC receptor induces pigment aggregation; and determining whether the pigment disposition in the test cells to which the second stimulant was added is changed from the initial state of pigment disposition. A control operation can also be performed. One example of a control operation is to introduce to the test cells in place of the second stimulant that activates the exogenous GPC receptor, a second stimulant that activates an endogenous GPC receptor that has the same effect on pigment disposition that activation of the exogenous GPC receptor would have. When no change in pigment disposition is seen in the test cells, while the control cells do undergo a change in pigment disposition, the chemical to be identified is an antagonist for the exogenous GPC receptor.

The present invention also concerns a method for identifying a chemical that acts as an antagonist for an exogenous PPG protein. The method comprises introducing to test cells of a pigment cell line capable of dispersing or aggregating their pigment in response to a specific stimulus and expressing an exogenous clone coding for the PPG protein, a first stimulant, e.g., a chemical or light, that sets an initial state of pigment disposition wherein the pigment is aggregated within the test cells if activation of the exogenous PPG protein induces pigment dispersion, or introducing a first stimulant, e.g., a chemical or light, that sets an initial state of pigment disposition wherein the pigment is dispersed within the test cells if activation of the exogenous PPG protein induces pigment aggregation; contacting the test cells set in an initial state of pigment disposition with the chemical to be identified; observing the cells to make determine that their state of pigment disposition remains unchanged; adding to the test cells contacted with the chemical to be identified, a second stimulant, that induces pigment dispersion by activating the exogenous PPG protein if activation of the exogenous PPG protein induces pigment dispersion, or adding a second stimulant that induces pigment aggregation by activating the exogenous PPG protein if activating the exogenous PPG protein induces pigment aggregation; and determining whether the pigment disposition in the test cells to which the second stimulant was added is changed from the initial state of pigment disposition. A control operation may also be performed. One example of a control operation is to introduce to the test cells in place of the second stimulant that activates the exogenous PPG protein, a second stimulant that activates an endogenous PPG protein that has the same effect on pigment disposition that activation of the exogenous PPG protein would have. When no change in pigment disposition is seen in the test cells, while the control cells do undergo a change in pigment disposition, the chemical to be identified is an antagonist for the exogenous PPG protein.

The present invention also concerns a method for identifying a chemical that acts as an agonist for an endogenous GPC receptor, e.g., one for serotonin that is endogenous to melanophores. The method comprises introducing to test cells of a pigment cell line capable of dispersing or aggregating their pigment in response to a specific stimulus and expressing an endogenous serotonin receptor, a stimulant, e.g., melatonin; contacting the test cells set in an initial state of pigment aggregation with the chemical; and determining whether the pigment in the test cells treated with the chemical is dispersed.

The present invention also concerns a method for identifying a chemical that acts as an antagonist for an endogenous GPC receptor, e.g., one for serotonin that is endogenous to melanophores. The method comprises introducing to test cells of a pigment cell line capable of dispersing or aggregating their pigment in response to a specific stimulus and expressing an endogenous serotonin receptor, a first stimulant, e.g., melatonin, that sets an initial state of pigment disposition wherein the pigment is aggregated within the test cells; contacting the test cells set in an initial state of pigment aggregation with the chemical to be identified; observing the cells to determine that their state of pigment disposition remains unchanged; adding to the test cells contacted with the chemical to be identified, a second stimulant, that induces pigment dispersion by activating the endogenous serotonin receptor; and determining whether the pigment in the test cells to which the second stimulant was added is dispersed. A control operation can also be performed. One example of a control operation is to introduce to the test cells in place of the second stimulant that activates the endogenous serotonin receptor, a second stimulant that activates another endogenous GPC receptor; e.g. the MSH receptor, that like the serotonin receptor induces pigment dispersion when activated. When no pigment dispersion is seen in the test cells, while the control cells do undergo pigment dispersion, the chemical to be identified is likely to be an antagonist for the endogenous serotonin receptor.

According to the present invention, a method is also provided for identifying a chemical that acts as an agonist for a PPG protein that is endogenous to melanophores; e.g., endogencus protein kinase A, protein kinase C, etc. The method comprises introducing to test cells of a pigment cell line capable of dispersing or aggregating their pigment in response to a specific stimulus and expressing an endogenous PPG protein, a stimulant, e.g., a chemical or light, that sets an initial state of pigment disposition wherein the pigment is aggregated within the test cells if activation of the PPG protein induces pigment dispersion, or introducing a stimulant, e.g., a chemical or light, that sets an initial state of pigment disposition wherein the pigment is dispersed within the test cells if activation of the PPG protein induces pigment aggregation; contacting the test cells set in an initial state of pigment disposition with the chemical; and determining whether the pigment in the test cells treated with the chemical is changed from the initial state of pigment disposition.

The present invention also concerns a method for identifying a chemical that acts as an antagonist for a PPG protein that is endogenous to melanophores; e.g., endogenous protein kinase A, protein kinase C, phosphodiesterase, etc. The method comprises introducing to test cells of a pigment cell line capable of dispersing or aggregating their pigment in response to a specific stimulus and expressing an endogenous PPG protein, a first stimulant, e.g., a chemical or light, that sets an initial state of pigment disposition wherein the pigment is aggregated within the test cells if activation of the PPG protein induces pigment dispersion, or introducing a first stimulant, e.g., a chemical or light, that sets an initial state of pigment disposition wherein the pigment is dispersed within the test cells if activation of the endogenous PPG protein induces pigment aggregation; contacting the test cells set in an initial state of pigment disposition with the chemical to be identified; observing the cells to determine that their state of pigment disposition remains unchanged; adding to the test cells contacted with the chemical to be identified, a second stimulant, that induces pigment dispersion by activating the endogenous PPG protein if activation of the endogenous PPG protein induces pigment dispersion, or adding a second stimulant that induces pigment aggregation by activating the endogenous PPG protein if activation of the endogenous PPG protein induces pigment aggregation; and determining whether the pigment disposition in the test cells to which the second stimulant was added is changed from the initial state of pigment disposition.

The present invention also provides a method for cloning GPC receptors. The method comprises introducing to pigment cells derived from a lower animal such as frogs and which are capable of continuous proliferation in vitro, exogenous nucleic acid clones; e.g., a cDNA library created in a plasmid vector, by any acceptable procedure; e.g. electroporation. The method then comprises introducing to the cells a stimulant, e.g., a chemical or light, that by activating an endogenous GPC receptor sets an initial state of pigment disposition within the cells; contacting the cells set in an initial state of pigment disposition with a chemical that activates the exogenous receptor; and identifying cells treated with the chemical whose pigment disposition is changed from the initial state of pigment disposition, whereby a change in pigment disposition indicates cells expressing the exogenous clone coding for the receptor.

The present invention also provides a kit for determining whether a chemical, e.g., a drug, acts as an agonist for an exogenous GPC receptor. The kit comprises in one or more containers: lower animal pigment test cells expressing an exogenous clone coding for the receptor; and a stimulant, e.g., melatonin, that induces pigment aggregation by activating an endogenous receptor if activation of the exogenous receptor induces pigment dispersion, and/or a stimulant, e.g., light or MSH, that induces pigment dispersion by activating an endogenous receptor if activation of the exogenous receptor induces pigment aggregation.

According to the present invention, there is further provided a kit for determining whether a chemical acts as an antagonist for an exogenous GPC receptor. The kit comprises in one or more containers: lower animal pigment test cells expressing an exogenous clone coding for the receptor; a first stimulant, e.g., melatonin, that induces pigment aggregation by activating an endogenous receptor if activation of the exogenous receptor induces pigment dispersion, and/or a first stimulant, e.g., light, that induces pigment dispersion by activating an endogenous receptor if activation of the exogenous receptor induces pigment aggregation; and a second stimulant that induces pigment dispersion by activating the exogenous receptor if activation of the exogenous receptor induces pigment dispersion, and/or a second stimulant that induces pigment aggregation by activating the exogenous receptor if activation of the exogenous receptor induces pigment aggregation.

The present invention also provides a kit for determining whether a chemical, e.g., a drug, acts as an agonist for an exogenous PPG protein. The kit comprises in one or more containers: lower animal pigment test cells expressing an exogenous clone coding for the protein; and a stimulant, e.g., melatonin, that induces pigment aggregation by activating an endogenous receptor if activation of the exogenous protein induces pigment dispersion, and/or a stimulant, e.g., light, that induces pigment dispersion by activating an endogenous receptor if activation of the exogenous protein induces pigment aggregation.

According to the present invention, there is further provided a kit for determining whether a chemical acts as an antagonist for an exogenous PPG protein. The kit comprises in one or more containers: lower animal pigment test cells expressing an exogenous clone coding for the protein; a first stimulant, e.g., melatonin, that induces pigment aggregation by activating an endogenous receptor if activation of the exogenous protein induces pigment dispersion, and/or a first stimulant, e.g., light, that induces pigment dispersion by activating an endogenous receptor if activation of the exogenous protein induces pigment aggregation; and a second stimulant that induces pigment dispersion by activating the exogenous protein if activation of the exogenous protein induces pigment dispersion, and/or a second stimulant that induces pigment aggregation by activating the exogenous protein if activation of the exogenous protein induces pigment aggregation.

The present invention also provides a kit for determining whether a chemical, e.g., a drug, acts as an agonist for an endogenous GPC receptor. The kit comprises in one or more containers: lower animal pigment test cells expressing the receptor; and a stimulant, e.g., melatonin, that induces pigment aggregation by activating an endogenous receptor if activation of the endogenous receptor to which the chemical is directed induces pigment dispersion, and/or a stimulant, e.g. light, that induces pigment dispersion by activating an endogenous receptor if activation of the endogenous receptor to which the chemical is directed induces pigment aggregation.

According to the present invention, there is further provided a kit for determining whether a chemical acts as an antagonist for an endogenous GPC receptor. The kit comprises in one or more containers: lower animal pigment test cells expressing the receptor; a first stimulant, e.g., melatonin, that induces pigment aggregation by activating an endogenous receptor if activation of the endogenous receptor to which the chemical is directed induces pigment dispersion, and/or a first stimulant, e.g., light, that induces pigment dispersion by activating an endogenous receptor if activation of the endogenous receptor to which the chemical is directed induces pigment aggregation; and a second stimulant that induces pigment dispersion by activating the endogenous receptor to which the chemical is directed if activation of the endogenous receptor to which the chemical is directed induces pigment dispersion, and/or a second stimulant that induces pigment aggregation by activating the endogenous receptor to which the chemical is directed if activation of the endogenous receptor to which the chemical is directed induces pigment aggregation.

The present invention also provides a kit for determining whether a chemical, e.g., a drug, acts as an agonist for an endogenous PPG protein. The kit comprises in one or more containers: lower animal pigment test cells expressing the protein; and a stimulant, e.g., melatonin, that induces pigment aggregation by activating an endogenous receptor if activation of the endogenous PPG protein induces pigment dispersion, and/or a stimulant, e.g., light, that induces pigment dispersion by activating an endogenous receptor if activation of the endogenous PPG protein induces pigment aggregation.

According to the present invention, there is further provided a kit for determining whether a chemical acts as an antagonist for an endogenous PPG protein. The kit comprises in one or more containers: lower animal pigment test cells expressing the protein; a first stimulant, e.g., melatonin, that induces pigment aggregation by activating an endogenous receptor if activation of the endogenous PPG protein induces pigment dispersion, and/or a first stimulant, e.g., light, that induces pigment dispersion by activating an endogenous receptor if activation of the endogenous PPG protein induces pigment aggregation; and a second stimulant that induces pigment dispersion by activating the endogenous PPG protein if activation of the endogenous PPG protein induces pigment dispersion, and/or a second stimulant that induces pigment aggregation by activating the endogenous PPG protein if activation of the endogenous PPG protein induces pigment aggregation.

In the above discussions as to what the invention does, reference is often made to the use of a "chemical or light" to set initial states of pigment disposition. In the experience of the inventors, working with melánophores from *Xenopus laevis,* the most convenient manner in which to set an initial state of pigment aggregation is to use melatonin while the most convenient manner in which to set an initial state of pigment dispersion is to use light. The reason for these choices is that in both cases their effects are readily and easily overcome by stimuli having the opposite effects on pigment disposition. This situation will not be the case for every type of chromatophore. For example, many fish melanophores respond to light by aggregating instead of dispersing their pigment while not responding to melatonin at all. If such melanophores were developed for use in the present invention, alternative initial stimuli would be used such as light for pigment aggregation and epinephrine for pigment dispersion. However, regardless of the actual chemicals or light and chromatophores involved in the assays the concepts are similar.

BRIEF DESCRIPTION OF THE DRAWINGS

FIG. 7 is a photograph showing that melanophores can express recombinant DNA, in this case by expressing cDNA coding for beta-galactosidase.

FIGS. 8A, 8B and 8C are a series of photographs showing that melanophores can express an exogenous human beta 2-adrenergic receptor and that when the receptor is stimulated, that the pigment cells disperse their pigment.

FIG. 14a shows an initial state of pigment disposition in a hypothetical field of cells; FIG. 14b shows the pigment disposition in the same field after treatment with a drug whose receptor is being cloned.

DETAILED DESCRIPTION OF THE INVENTION

Overview

Figure 1:
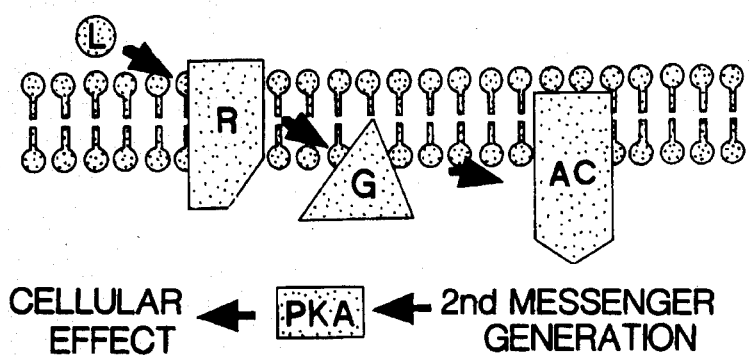
FIG. 1 is a schematic drawing showing one example of a signal transduction pathway utilizing G-proteins and second messengers, in this case cAMP.

The present invention takes advantage of the development of special lines of pigment cells that can be continuously propagated in vitro and which can dramatically alter their appearance in response to stimulation of proteins participating in signal transduction pathways that utilize G-proteins and/or second messengers, e.g., cyclic adenosine monophosphate (cAMP).

Applicants have designed an accurate and straightforward bioassay that can be used to screen literally thousands of chemicals in a single day to evaluate their abilities to activate or block GPC receptors and other PPG proteins. Examples of GPC receptors that can be studied include beta 2-adrenergic receptors, bombesin receptors and serotonin receptors. Examples of other PPG proteins that can be studied include adenyl cyclase and protein kinase C.

The major asset of the invention is its ability to vastly increase over current methods, the rate at which potential drugs can be evaluated for their ability to act as agonists or antagonists for GPC receptors. In essence, a cDNA clone coding for a GPC receptor, e.g., beta 2-adrenergic receptor, is introduced into pigment cells by any of several standard procedures; e.g., electroporation. Cells which are either transiently or permanently expressing the receptor form the basis of a bioassay for evaluating the ability of chemicals to be either agonists or antagonists for beta 2-adrenergic receptors by observing how the addition of chemicals to the cells affects the state of pigment disposition within the cells. In a similar manner, the cells can also be used to evaluate chemicals as potential agonists or antagonists for GPC receptors that are already present on the pigment cells. Finally, the cells can also be used to evaluate chemicals as potential agonists or antagonists for PPG proteins that are already present on the pigment cells.

Applicants have further designed a method for cloning cDNAs coding for GPC receptors. For example, there are two known types of glucagon receptors, both of which are GPC receptors (Wakelam, M. J. O., Murphy, G. J., Hruby, V. J. and Houslay, M. D. (1986) *Nature*, 323:68–71). One of them activates a signal transduction pathway that mediates intracellular levels of cAMP while the other mediates levels of IP3. Both of these receptors can be cloned by the new methodology since stimulation of either pathway induces pigment dispersion. The present invention uses molecular biological methods to transfect pigment-containing cells with a plasmid or viral based cDNA library derived from the mRNA present in a tissue or cell line that expresses a receptor of interest, in this case glucagon. An imaging system, e.g., a computer guided video system, or even photographs, can be used to identify pigment cells that disperse their pigment granules—melanosomes—in response to glucagon. Once reactive cells are found, several well-known approaches can be used to clone a receptor of interest.

Cells

Cultures of melanophores have been obtained. Continuous long term cultures of melanophores have been established (Ide (1974), *Developmental Biology*, 41: 380–384). Cultures derived from *Xenopus laevis* used by applicants were established (Daniolos et al. (1990), *Pigment Cell Research*, 3:38–43), have gone through over 100 cell population doublings, and continue to steadily divide approximately every 5 days. Applicants have further established and characterised several pure clonal sublines for such aspects as to their rates of growth, degree of pigmentation and sensitivity of pigment disposition to stimulating agents such as light and melatonin.

Stimulants

Agents which affect GPC receptors or PPG proteins induce dramatic changes in melanophores. Based on experiments with intact animals, skin and cultured cells, it has been known for many years that several types of chromatophores from various animals, and melanophores in particular, respond to a number of agents by either dispersing or aggregating their melanosomes (Lerner and Case (1959), *Investigative Dermatology*, 32: 211–221; Butman et al. (1979), *J. Exp. Zool.*, 208: 17–34; and Hogben and Slome (1931) *Proc. Royal Soc. B.*, 108: 10–53). An example of a chemical which induces pigment dispersion includes melanocyte stimulating hormone (MSH). Melatonin on the other hand, causes pigment aggregation. Some agents, such as norepinephrine induce pigment dispersion in melanophores from one type of frog such as *Xenopus laevis*, but aggregation in those from another species such as *Rana pipiens*. It turns out that melanophores from *Xenopus laevis* have beta-adrenergic receptors but lack significant numbers of alpha-adrenergic receptors, while those from *Rana pipiens* have both beta and alpha-receptors. Interestingly, while melanophores from one source, such as ours, remain constant in terms of what receptors are expressed, there can be stable genetic differences even within a single species. For example, the melanophores in some *Rana pipiens* aggregate their pigment granules on exposure to acetylcholine while those from other *Rana pipiens* do not respond to the chemical (Moller and Lerner (1966), *Acta Endocrinologica*, 51: 149–160). It is now known that any agent that causes an increase in intracellular cAMP causes pigment dispersion (Rozdzail and Haimo (1986), *Cell*, 47: 1061–1070; Lynch et al. (1986), *J. Biol. Chem.*, 261: 4212–4216).

Figure 2A:
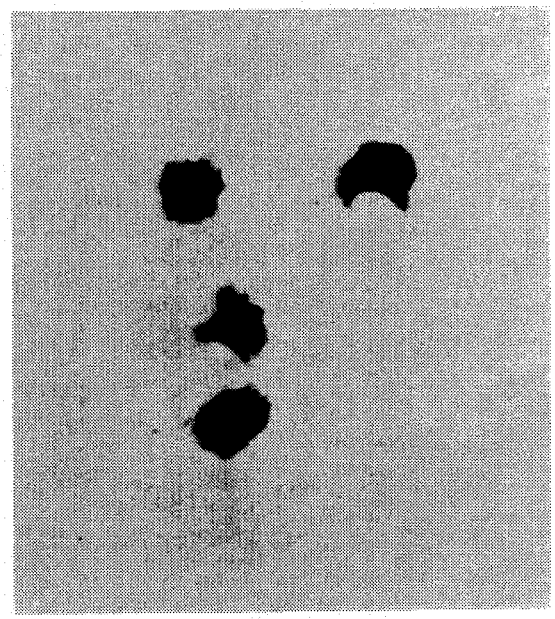
FIG. 2a is a photograph showing cells treated with melatonin.
Figure 2B:
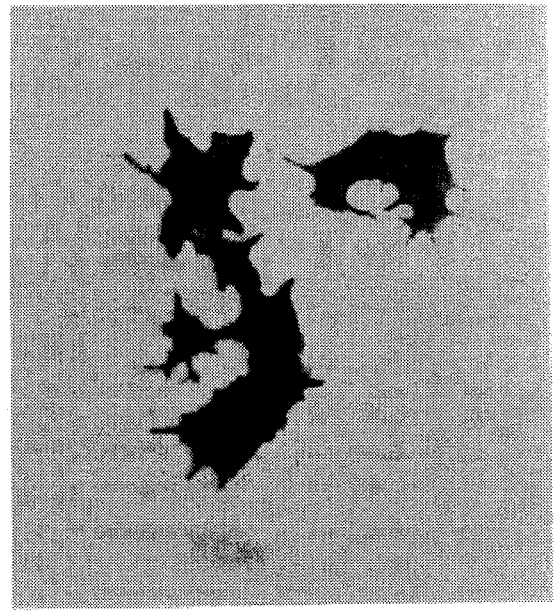
FIG. 2b is a photograph showing the same cells depicted in FIG. 2a treated with MSH.

Applicants have tested the ability of *Xenopus laevis* melanophores to respond to several chemicals and FIG. 2 demonstrates the effects of melatonin and MSH on four cells. The effect of treating the cells with 0.1 nM melatonin for 30 minutes is shown in the left side of FIG. 2 while the right side shows the same cells following exposure to 100 nM MSH for an additional 30 minutes (in the continued presence of the melatonin). Cells that are not exposed to either melatonin or MSH will vary in their degrees of pigment aggregation and dispersion (data not shown).

While it is known that MSH, melatonin and drugs that activate beta 1-adrenergic receptors can affect melanophores, applicants have also found that melanophores from *Xenopus laevis* disperse their pigment in response to seronomin. This finding is significant because the literature reports the opposite effect (Messenger and Warner (1977) *Br. J. Pharmcology* 61:607–614). On the other hand, applicants have also found that their cells do not respond with any change in pigment disposition to many of the chemicals which affect receptors belonging to the GPC class such as beta 2-adrenergic, bombesin or substance P receptor selective agonists. Some of applicants' results are summarized in Table 1.

Table 1 provides a partial list of chemicals and light that induce pigment translocation in applicants melanophores

TABLE 1

| Reagent | Effect on Melanosomes |
| --- | --- |
| A 0.1 nM melatonin followed by | aggregation |
| 10 nM MSH | dispersion |
| 10 nM (-)isoproterenal | dispersion |
| 1 µM norepinephrine | dispersion |
| 460 nm light | dispersion |
| 100 nM serotonin | dispersion |
| 100 uM metaproterenol | no response |
| 1 µM bombesin | no response |
| 1 µM substance P | no response |
| 1 µM dopamine | no response |
| B 3 nM MSH followed by | dispersion |
| 100 nM melatonin | aggregation |
| 100 µM clonidine | no response |
| 100 µM p-aminoclonidine | no response |
| 100 µM phenylephrine | no response |

Figure 3:
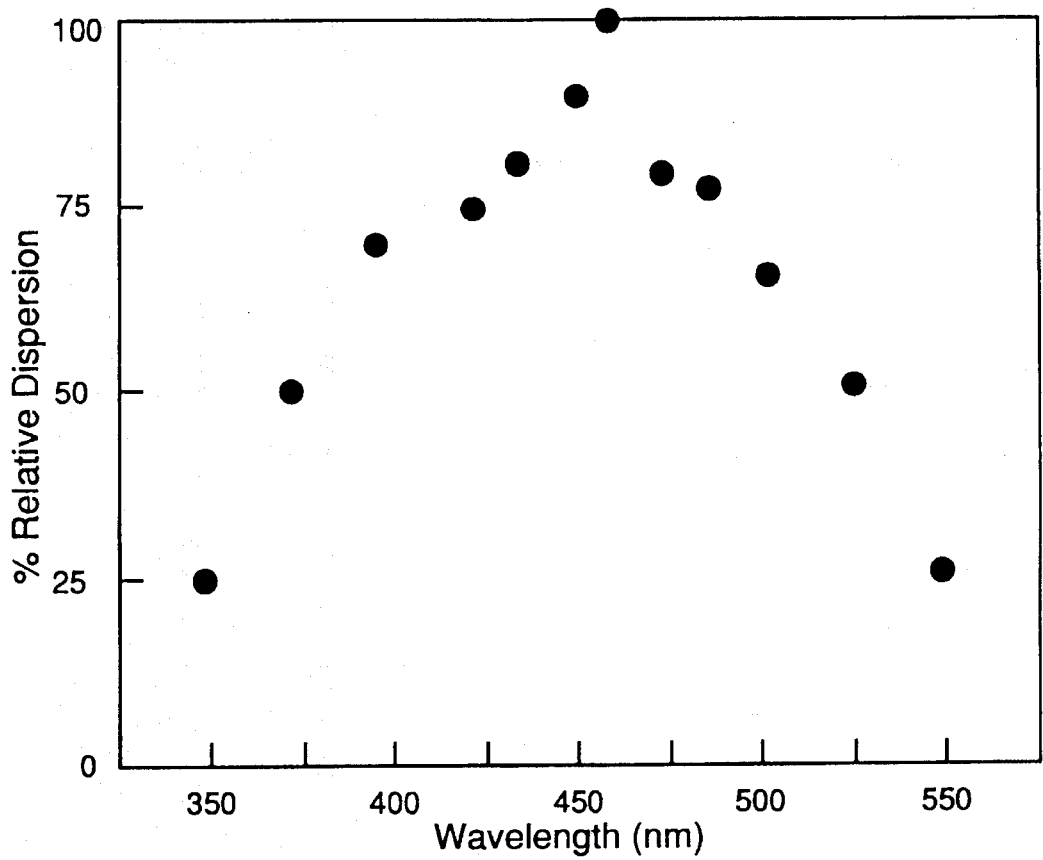
FIG. 3 is a plot of % relative dispersion vs. wavelength of light stimulation which shows the spectral sensitivity of cultured melanophores from *Xenopus laevis*. Melatonin aggregated melanophores were stimulated for 10 minutes with light of various wavelengths using a PTI grating monochromator. The relative sensitivities of melanophores to different wavelengths were adjusted to give a value of 100% for 460 nm.

Light induced melanosome dispersion is mediated by a G-protein based signal transduction pathway. In the case of melanophores from *Xenopus laevis*, the pathway uses cAMP as its second messenger. This finding is fascinating from the standpoint that phototransduction in the melanophores is mediated by a different second messenger system than the cGMP based one use in the vertebrate visual system (Stryer, L. (1986) *Ann. Rev. Neurosci.*, 9: 87–119). However, the major point here is that the pigment cells' photosensitivity can be used to set the cells in a state of pigment dispersion in a very simple manner and is useful in screening for chemicals that cause pigment aggregation. FIG. 3 depicts the spectral sensitivity of cultured melanophores from *Xenopus laevis*. Melanophores with aggregated pigment as a consequence of exposure to melatonin were stimulated for 10 minutes with light of various wavelengths using a PTI grating monochromator. The relative sensitivities of melanophores to different wavelengths were adjusted to give a value of 100% for 460 nM. As shown in FIG. 3, when cells are exposed to a range of wavelengths of light at constant intensities, the cells are maximally sensitive to light of 460 nm and are insensitive to light above 550 nm. As 550 nm is within the visual range, handling the melanophores without triggering photoresponse is not difficult.

Quantifying Pigment Disposition

Figure 4A:
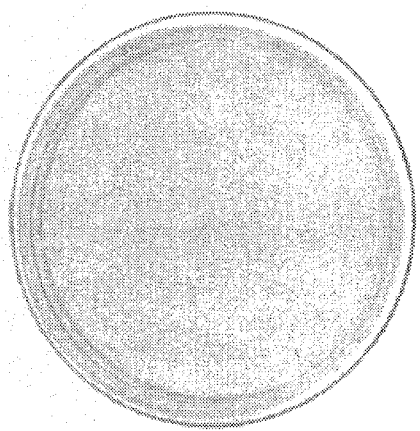
FIGS. 4a and 4b are photographs which provide a comparison between the difference in opacity exhibited by confluent cells whose pigment granules are aggregated or dispersed.
Figure 4B:
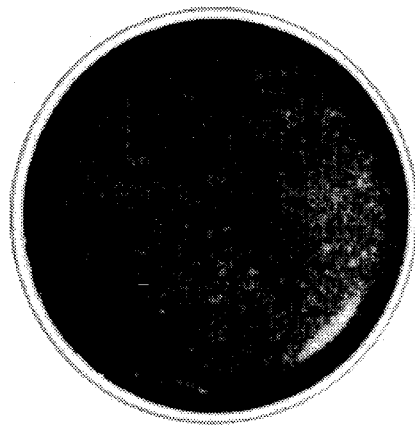

FIGS. 4a and 4b provide a comparison between the difference in opacity exhibited by confluent cells whose pigment granules are aggregated or dispersed. FIG. 4a shows a 100 mm tissue culture dish with confluent melanophores that has been treated with 0.1 nM melatonin for 30 minutes. FIG. 4b shows another dish containing the same number of melanophores but it received 100 nM MSH for 30 minutes following the treatment with melatonin.

Figure 5:
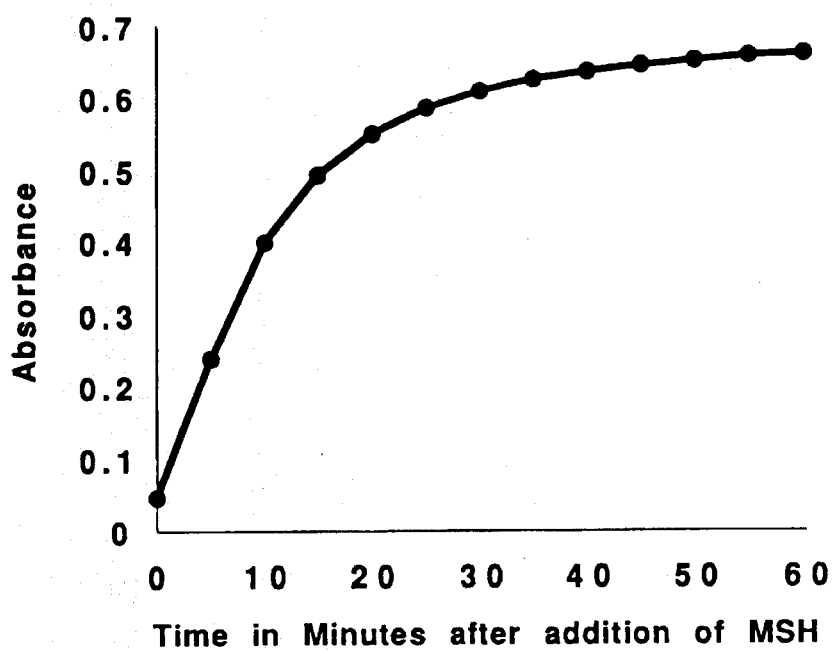
FIG. 5 is a plot of the change in degree of absorbance vs. time by a well of a 96 well plate containing confluent melanophores that were first set in a state of pigment aggregation with melatonin and then treated with MSH.

The melanophore assay according to the present invention can be read with a standard 96 well plate reader. Although the ability of a chemical to induce pigment dispersion or aggregation within melanophores can be easily recognized by eye, for a rapid drug screen, quantitation of the degree of pigment dispersion, e.g., with a standard 96 well plate, is useful. FIG. 5 graphically displays the results of pigment dispersion within melanophores in response to chemical stimulation within a well of a 96 well microtiter plate. To obtain this curve, the well, which contained a confluent layer of melanophores, was first treated with 10 nM melatonin for 1 hour. The absorbance of light at 620 nM (a wavelength not detected by the cell's endogenous photoreceptor) was then determined. Next, MSH was added to 100 nM and the absorbance of 620 nM light by the well was measured every 5 minutes for one hour.

Figure 6A:
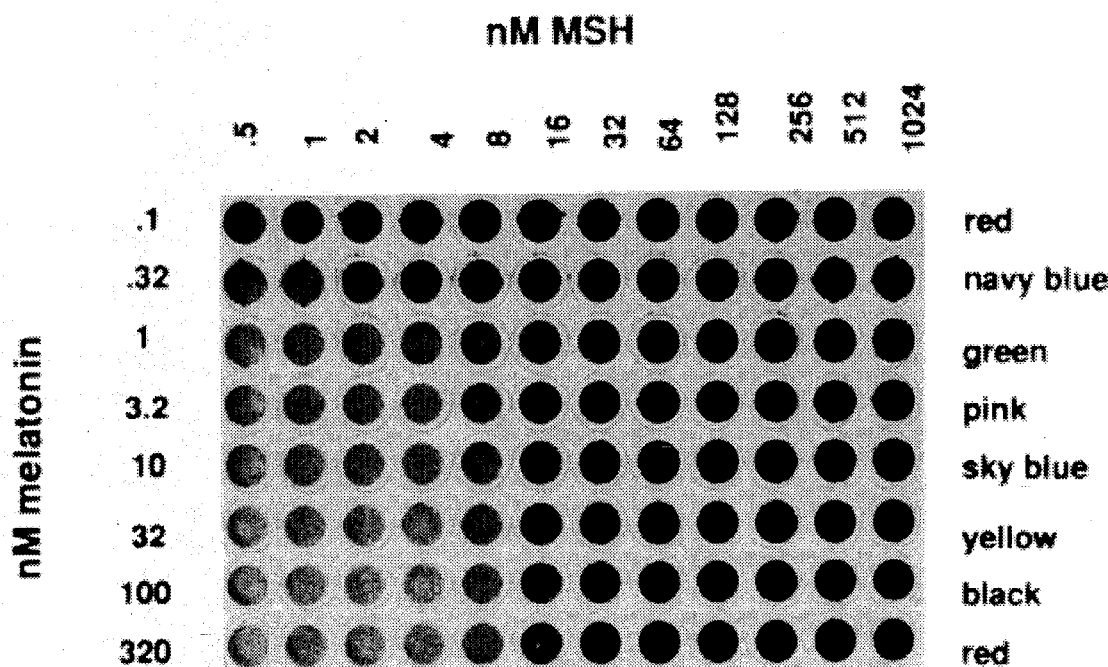
FIG. 6a is a photographic display of dose response curves for melanophores in a 96 well plate where each well was treated with a distinct combination of melatonin and MSH.
Figure 6B:
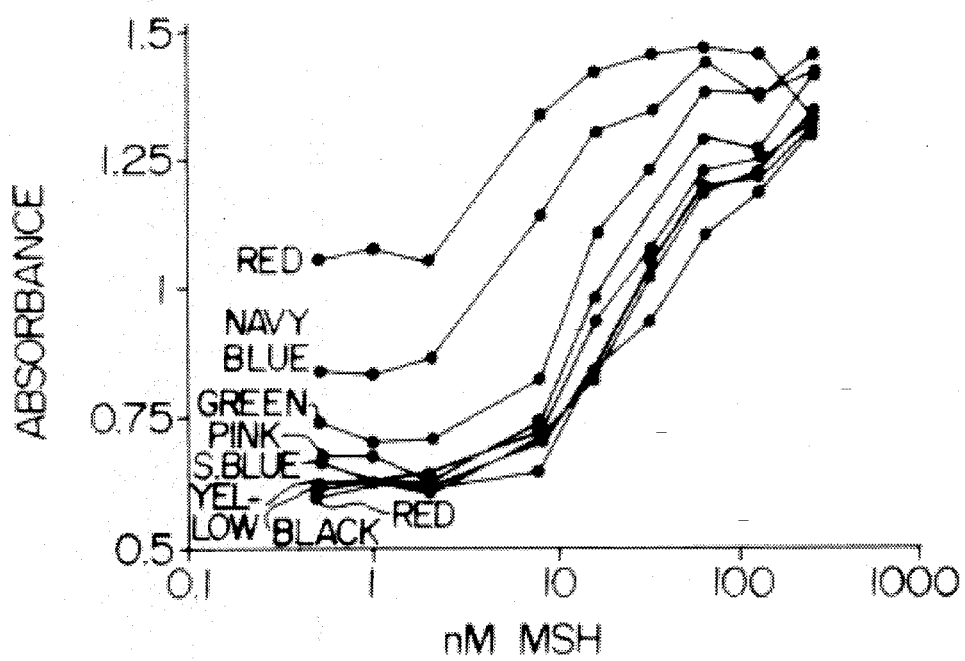
FIG. 6b is a graphical display of the same information as in FIG. 6a as converted by a microtiter plate reader.

The melanophore assay according to the present invention can be used to rapidly determine dose responses to chemicals that interact with GPC receptors and other PPG proteins. FIG. 6 demonstrates this point with the MSH receptor that is endogenous to the pigment cells. In FIG. 6a a microtiter plate is shown in which each well has been treated with a different combination of melatonin and MSH. First 8 different doses of melatonin were added by row to final concentrations ranging between 0.1 and 320 nM. After 60 minutes, the wells were then given by column, one of 12 different doses of MSH ranging between 0.5 and 1,024 nM. After thirty minutes the plate was read with a microplate reader and then fixed. The fixed plate is shown in the photograph of FIG. 6a while the dose response curves representing the rows from top to bottom as determined by the microplate reader are depicted in FIG. 6b. The plate reader can reliably distinguish between wells receiving different concentrations of chemicals.

Expression of Exogenous GPC Receptors in Melanophores

The first step in developing a melanophore based methodology for studying the affects of chemicals on GPC receptors has been to determine how to express foreign DNA in the cells. Several promoters and procedures for DNA transfection have been tested for their ability to be used by frog melanophores to express foreign cDNAs. The tested promoters include ones from CMV (cytomegalovirus), RSV (rous sarcoma virus), frog heat shock, SV-40 early and frog beta-actin while the tested methods of introducing DNA into the cells that have been evaluated include calcium phosphate precipitation, DEAE-dextran, lipofection and electroporation (Hall, C. V., Jacob, P. E., Ringold, G. M. and Lee, F. (1983), *J. Mol. Appl. Genet.*, 2: 101–109; Harland, R. and Misher, L. (1988) *Development*, 102: 837–852; Gorman, C. M., Merlino, G. T., Willingham, M. C., et al. (1982), *Proc. Natl. Acad. Sci.* 22: 6777–6781; Spaete, R. R. and Mocarski, E. S. (1985), *Journal of Virology*, 56: 135–143; Sambrook, J., Fritsch, E. F. and Maniatis, T. (1989) *Molecular Cloning*, Cold Spring Harbor Laboratory Press 2nd. ed. 1610–1612; McCutchan, J. H. and Pagano, J. S. (1968), *J. Natl. Cancer Inst.*, 41: 351–357; Warden, D. and Thorne, H. V. (1968), *J. Gen. Virol.* 3: 371–377; Felgner, P. L., Gadek, T. R., Holm, M., et al. (1987), *Proc. Natl. Acad. Sci.* 84: 7413–7417; Boggs, S. S, Gregg, R. G., Borenstein, N. and Smithies, O. (1986), *Exp. Hematol.*, 14: 988–994). The best combination appears to be the use of a CMY promoter to drive expression of a cDNA of interest along with electroporation. An example of using electroporation to introduce a plasmid containing a lacZ gene coding for beta-galactosidase behind a CMV promoter into pigment cells is shown in FIG. 7. The cells have been treated with melatonin in order to aid in the visualization of beta-galactosidase via an X-gal stain in their cytoplasm. The efficiency of transfection in this particular experiment was 63%. In an average experiment the efficiency is 37%.

The next step in developing the pigment cell cDNA expression system for use in drug screening has been to demonstrate that a characterized seven transmembrane domain receptor that activates a G-protein based signal transduction pathway and was normally expressed by human beings could be appropriately expressed in frog melanophores. In order to evaluate this important point, the human beta 2-adrenergic receptor was chosen since applicants knew that the frog pigment cells did not respond to the beta 2-receptor specific drug metaproterenol (see Table 1). Two criteria had to be met. First, the receptor had to be expressed by a significant number of cells. Second, receptor expressed by transfected cells had to be capable of coupling to endogenous Gs.

FIG. 8 presents a demonstration that the aforementioned criteria 1 and 2 have been met. In the first panel, pigment cells are shown that were transfected two days previously in an electroporation experiment using 40 μg of plasmid coding for the human beta 2-receptor arranged behind a CMV promoter. Here the cells have been treated with 10 nM melatonin for 60 minutes to aggregate pigment. The second panel shows the identical field of cells taken as a multiple exposure that was made in the following manner.

First, the cells were exposed to red light but the film in the camera was not advanced. Second, the cells were treated with 1 μM metaproterenol for 30 minutes. Third, the cells were exposed to white light.

Any cell that dispersed its pigment in response to metaproterenol should block white light from hitting the film although it had already allowed red light to pass. The result would be that cells that dispersed their pigment in response to metaproterenol would appear as red with dark centers.

Meanwhile, any cell that had not received the beta 2-receptor plasmid would not disperse its pigment in response to metaproterenol and hence appear as only a small dark spot because any area of film exposed to both red and white light would appear white. The final panel shows the same cells again but as a single exposure following treatment with metaproterenol. In this experiment the percentage of cells that gained the ability to respond to metaproterenol was the same as applicants' average transfection efficiency. This demonstrates that a receptor originally derived from human beings is capable of functionally coupling to a G-protein mediated signal transduction pathway in frog pigment cells.

Figure 9:
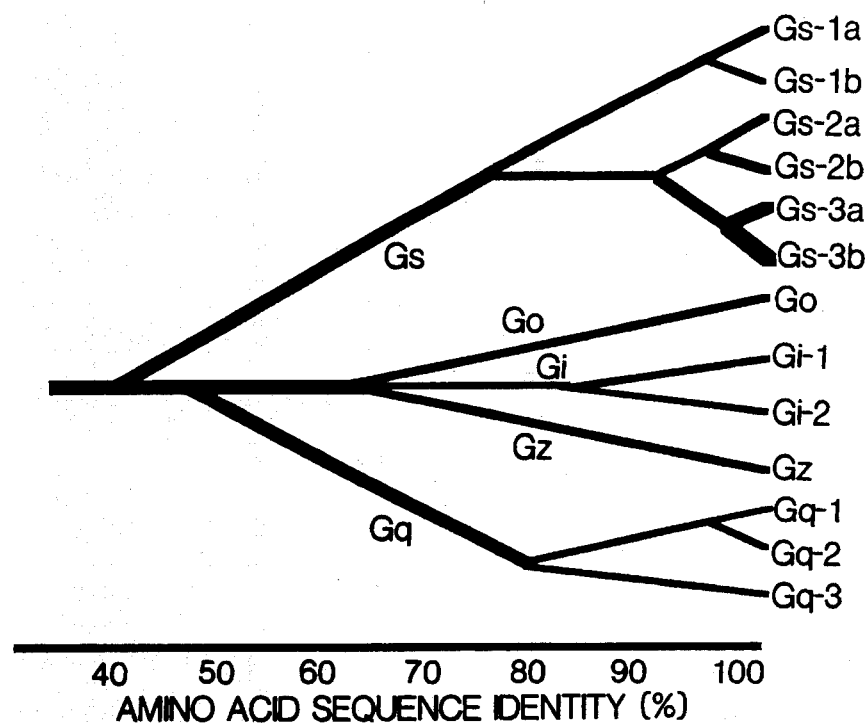
FIG. 9 is a schematic drawing showing different subunits of G-proteins known to be expressed in the pigment cells.

Applicants have also demonstrated that other G-protein mediated signal transduction pathways can control pigment translocation within frog melanophores based on several criteria. First, the cells have numerous distinct G-proteins as shown in FIG. 9. In fact the pigment cells have multiple G-proteins from every class. Second, three other exogenous GPC receptors have been expressed in frog melanophores (data not shown). These include receptors for serotonin, bombesin and substance P. In every case, addition of an appropriate agonist induced pigment dispersion. The importance of these studies is that the bombesin and substance P receptors, while exerting their effects via a G-protein mediated signal transduction pathway, utilize different ones from that utilized by the beta 2-adrenergic receptor. Third, the calcium ionophore A23187 (Pressman, B. C. (1976) *Ann. Rev. Biochem.* 45: 501–530) also induces pigment dispersion (data not shown). Fourth, the agent TPA, which is known to stimulate protein kinase C, induces pigment dispersion (data not shown).

It should be possible for any GPC receptor expressed in pigment cells via transfection, to induce pigment translocation. As discussed above, the pigment cells have many endogenous G proteins. While is unlikely to be the case that all of them couple GPC receptors to the pigment translocation mechanism in the cells, many of them must. Also, additional ones can be added by expressing exogenous ones via the type of recombinant DNA technology used to express GPC receptors in the melanophores. Finally, it is possible to construct in vitro, and then express in the melanophores, chimeric G-proteins that will allow GPC receptors that normally couple to a G-protein based pathway that does not lead to pigment translocation to one that does. The importance of these points is that any GPC receptor will be capable of inducing pigment translocation apon stimulation when the cells are made to express a G-protein that can couple it to a signal transduction system regulating pigment translocation.

Bioassays for Evaluating Potential Agonists and Antagonists for Exogenous GPC Receptors The preliminary step of the bioassay methods of the present invention is to express exogenous cDNA in melanophores from *Xenopus laevis*. For clarity, the human beta 2-adrenergic receptor is used as an example. However, the descriptions apply equally well too any GPC receptor whose coding DNA has been cloned, such as thyrotropin, lutropin-choriogonadotropin, dopamine and histamine receptors etc. Likewise, once clones are available for other GPC receptors, such as those for glucagon, the assays described below.

Significance to the Drug Design and Discovery Process

Technologies for finding chemicals which affect GPC receptors and other PPG proteins and for cloning GPC receptors are important for both medicine and biology. The methods of the present invention provide: (1) a potent method for rapidly and carefully screening for new drugs affecting GPC receptors and other PPG proteins, and (2) a potent method for cloning new GPC receptors and for probing how the receptors work. As additional GPC receptors genes are characterized and site directed mutagenesis is used to analyze them, detailed knowledge will be gained about the basic mechanisms at work in these receptors. A fundamental knowledge of the basic mechanisms at work in these receptors will be of great use in understanding how to develop promising new drugs.

The present invention can also be used to test for drugs, e.g., narcotics, e.g. cocaine, heroin, morphine or designer opiates in foods or bodily fluids, e.g., blood or urine.

EXAMPLES 1: A FIRST BIOASSAY

A Bioassay for Evaluating Potential Agonists for the Human beta 2-Adrenergic Receptor or Another GPC Receptor Whose Activation Leads to Pigment Dispersion.

Figure 10:
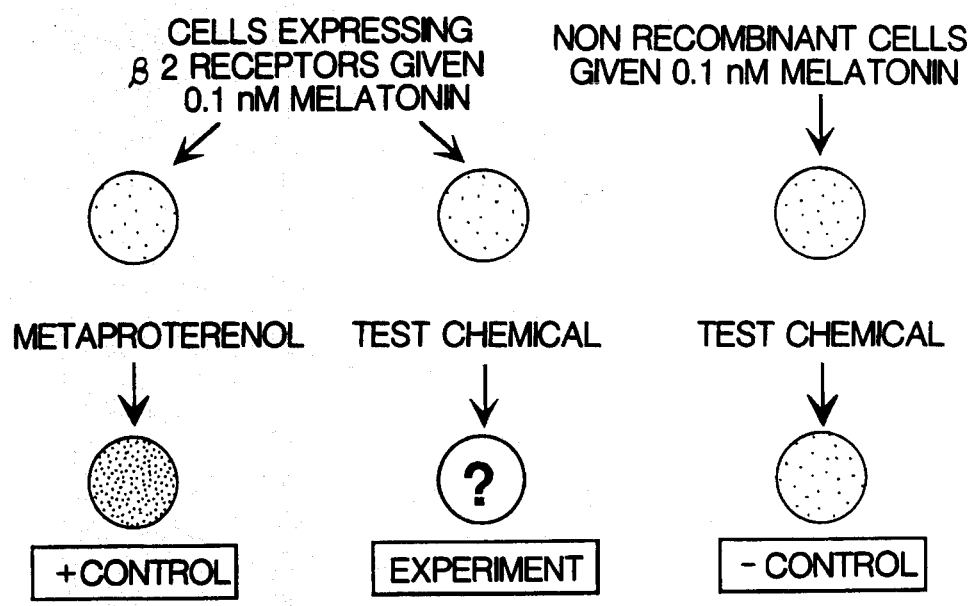
FIG. 10 is a schematic diagram of a beta 2-adrenergic receptor agonist assay.

To screen for new drugs that stimulate the β2-adrenergic receptors, recombinant melanophores that express the receptor and nonrecombinant ones that do not, are set up in sets of tissue culture wells as depicted in FIG. 10. All wells are treated with 0.1–1 nM melatonin to induce intracellular pigment aggregation. This concentration of melatonin can be easily overcome with small doses of chemicals such as isoproterenol (which stimulates the melanophores endogenous beta 1-adrenergic receptors) or MSH.

As seen in the first column in FIG. 10, a selective beta 2-receptor agonist such as metaproterenol is used as a positive control where a well containing beta 2-receptor bearing cells will turn dark due to pigment dispersion. Chemicals to be tested are simultaneously applied to other sets of wells, as depicted in columns 2 and 3 of FIG. 10, which respectively contain melanophores expressing beta 2-receptors and the nonrecombinant parent cell line.

A potentially interesting chemical would be one that, like metaproterenol, induced pigment dispersion in the recombinant cells, but which had no effect on the standard ones.

When a promising chemical is identified, it can be further characterized in at least two ways. First, the speed with which different concentrations induce pigment dispersion can be compared with the dose response for an established drug like metaproterenol. And second, if melanophores expressing other GPC receptors are available, the degree of specificity versus cross reactivity with these receptors can be ascertained.

EXAMPLE 2: A SECOND BIOASSAY

A Bioassay for Evaluating Potential Antagonists for the Human beta 2-Adrenergic Receptor or Another GPC Receptor Whose Activation Leads to Pigment Dispersion.

Figure 11:
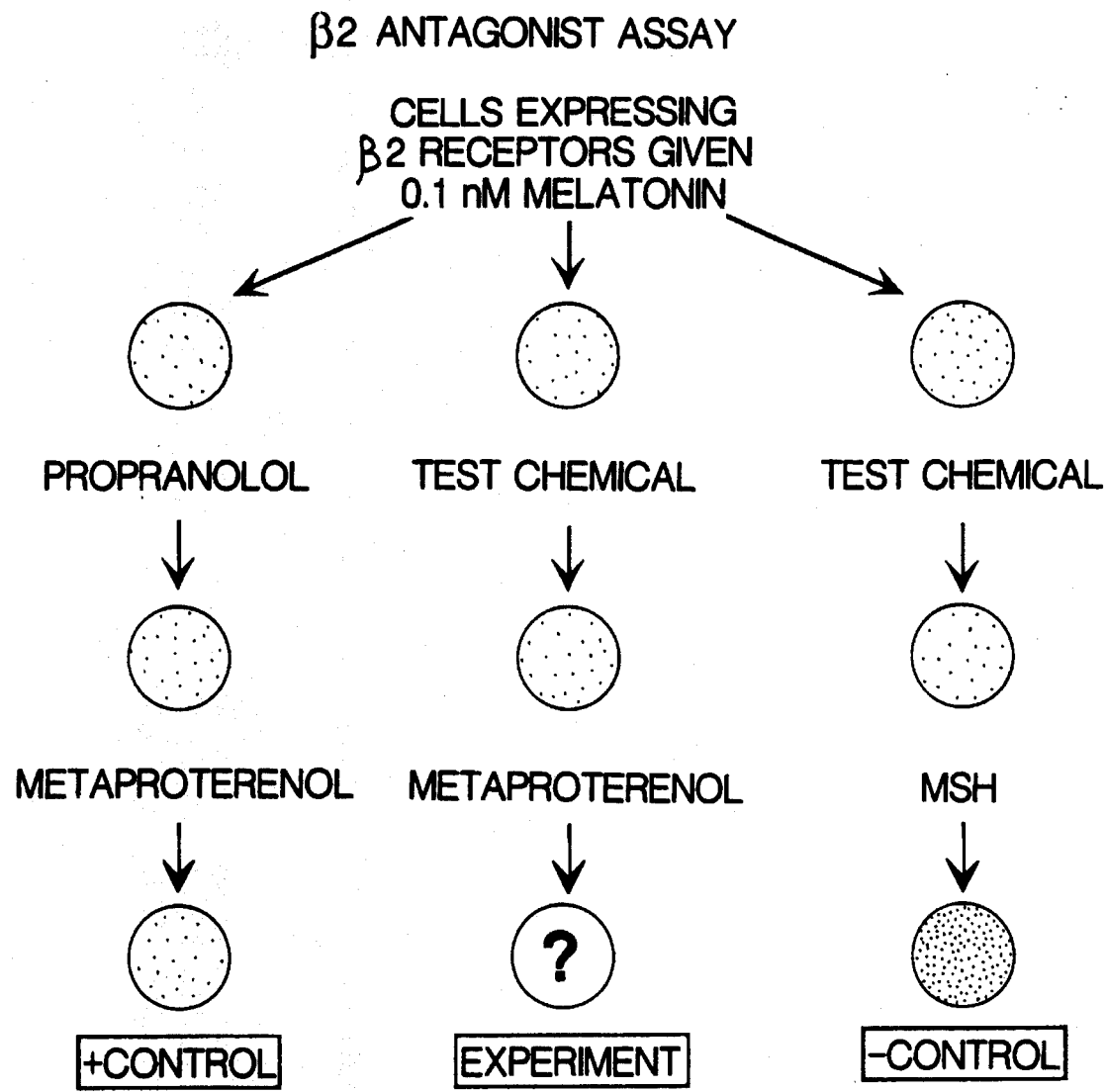
FIG. 11 is a schematic diagram of a beta 2-adrenergic receptor antagonist assay.

To screen for new drugs that antagonize beta 2-adrenergic receptors, melanophores expressing the receptor will be set up in parallel sets of tissue culture wells as outlined in FIG. 11. As with the strategy for identifying beta 2-adrenergic receptor agonists, all wells will be given 0.1–1 nM melatonin to induce intracellular pigment aggregation. A beta-adrenergic receptor antagonist such as propranolol is then applied as a positive control (column 1). The beta-receptor blocker prevents the cells from dispersing their pigment following the addition of the beta 2-adrenergic receptor selective stimulant metaproterenol, New chemicals to be tested are applied to other sets of wells.

A promising chemical is one that like propranolol prevents pigment dispersion in response to metaproterenol, but which does not prevent pigment darkening induced by an agent such as MSH which stimulates another GPC receptor on the cells as seen in columns 2 and 3. The negative control is used both to make sure that the chemical in question is not preventing pigment dispersion simply by damaging the cells, and also to ascertain that the blockade of metaproterenol induced pigment dispersion is not occuring at some more fundamental level in the cAMP cascade beyond the beta 2-adrenergic receptor. An example of the latter would be a chemical which directly inhibited adenylate cyclase. When an interesting chemical is found, it is further characterized for both receptor specificity and potency as described in the case of evaluating new beta 2-adrenergic receptor agonists.

EXAMPLE 3: A THIRD BIOASSAY

A Bioassay for Evaluating Potential Agonists for the Human α2-Adrenergic Receptor or Another GPC Receptor Whose Activation Leads to Pigment Aggregation (Jakobs (1979), *Molecular and Cellular Endocrinology* 16: 14T–156)

Figure 12:
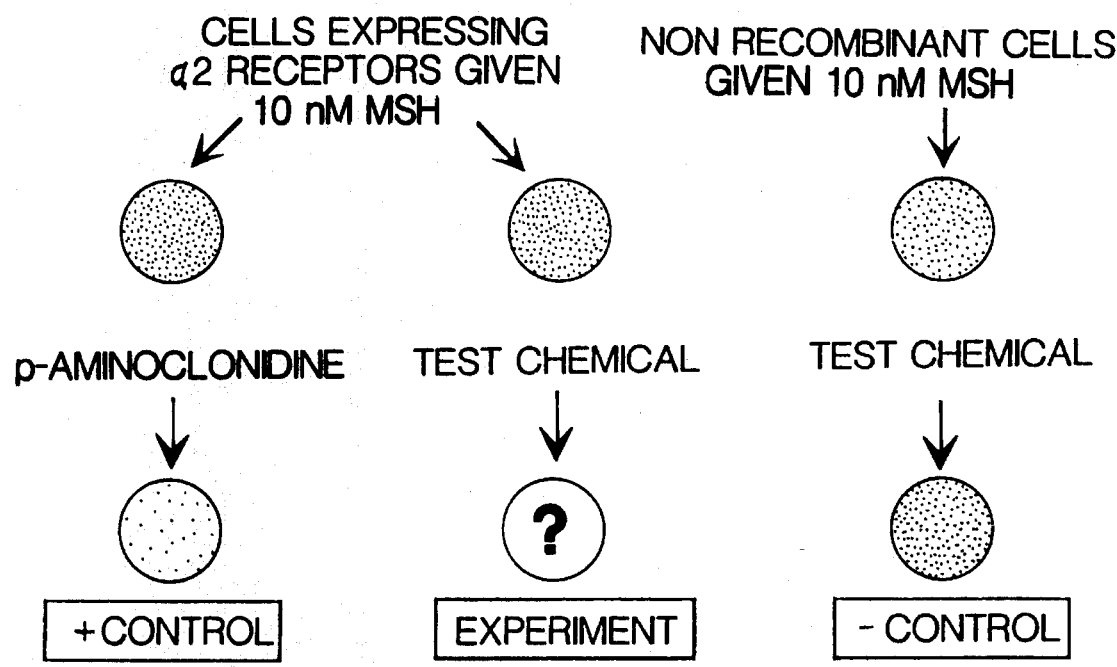
FIG. 12 is a schematic diagram of a alpha 2-adrenergic receptor agonist assay.

To screen for new drugs that stimulate alpha 2-adrenergic receptors, the assay is almost identical to the one described beta 2-adrenergic receptor agonists, except that it begins with dark wells instead of light ones. Recombinant melanophores expressing the receptor and nonrecombinant ones lacking the receptor, are set up in parallel sets of tissue culture wells as outlined in FIG. 12. All wells are exposed to light or given a small amount of a chemical such as MSH to induce intracellular pigment dispersion. An alpha 2-adrenergic receptor selective agonist such as p-aminoclonidine serves as a positive control.

Like the effect of melatonin, p-aminoclonidine should induce the recombinant cells to lower their intracellular concentrations of cAMP and aggregate their melanosomes. Chemicals to be tested will be applied to other sets of wells, some of which contain recombinant melanophores and some of which contain standard ones as shown by columns 2 and 3.

An interesting chemical would be one that induced pigment aggregation in alpha 2-adrenergic receptor positive cells, while having no effect on the parent cells. A potentially useful chemical can be further characterized for its receptor specificity and potency as described in section a for evaluating beta 2-receptor agonists.

EXAMPLE 4: A FOURTH BIOASSAY

Figure 13:
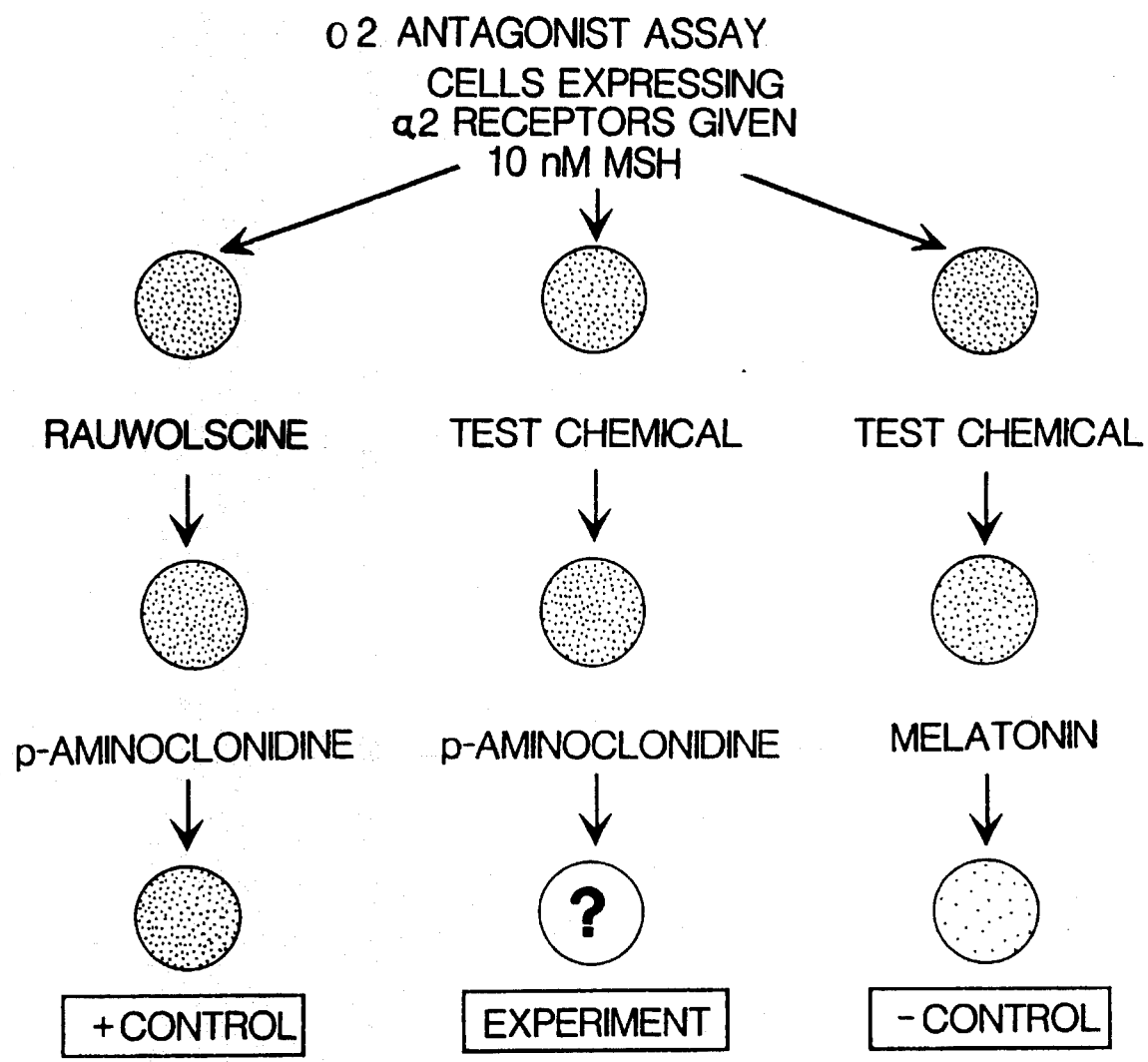
FIG. 13 is a schematic diagram of a alpha 2-adrenergic receptor antagonist assay.

A Bioassay For Evaluating Potential Antagonists For The Human alpha 2-Adrenergic Receptor or Another GPC Receptor Whose Activation Leads to Pigment Aggregation The assay for new drugs that antagonize alpha 2-receptors begins with wells containing recombinant melanophores expressing alpha 2-receptors that have been darkened by light or a chemical such as MSH as outlined in FIG. 13. An alpha 2-receptor antagonist such as rauwolscine will serve as a positive control as it prevents the agonist p-aminoclonidine from inducing pigment aggregation. New substances are applied to parallel wells and a potentially interesting chemical is one that like rauwolscine, blocks p-aminoclonidine but not melatonin induced pigment aggregation. As before, the selectivity and potency of promising molecules is further characterized as described in the case of evaluating beta 2-adrenergic receptor agonists.

EXAMPLE 5: A FIFTH BIOASSAY

A Bioassay for Evaluating Potential Agonists of the Endogenous Serotonin Receptor To screen for new drugs that stimulate the endogenous serotonin receptor, melanophores are set up on sets of tissue culture wells. All wells are treated with 0.1–1 nM melatonin to induce intracellular pigment aggregation. This concentration of melatonin is easily overcome with small doses of chemicals such as isoproterenol (which stimulates the melanophores endogenous beta 1-adrenergic receptors) or MSH. Serotonin is used as a positive control where a well turns dark due to pigment dispersion. Chemicals to be tested are simultaneously applied to other sets of wells. A potentially interesting chemical would be one that, like serotonin, induced pigment dispersion in the cells. When a promising chemical is identified, it can be further characterized by the speed with which different concentrations induce pigment dispersion as compared with the dose response for an established chemical like serotonin.

As a specificity control for a promising compound, a serotonin receptor antagonist can be added prior to the addition of the promising compound. If pigment dispersal following the addition of the promising compound is now prevented, it is likely that the new compound is a specific agonist for serotonin receptors.

For all of the assays described hereinbefore, it should be clear that melanophores expressing exogenous GPC receptors and other PPG proteins either transiently or permanently can be used.

EXAMPLE 6: ISOLATING cDNA CLONES CODING FOR GPC RECEPTORS

Frog melanophores can form the basis of a method for cloning GPC receptors by rapidly screening a cDNA library. The key to cloning a GPC receptor is to be capable of rapidly screening random cDNA clones from a library in order to find one coding for the receptor of interest. Here, the murine bombesin receptor is used to provide an example of how at least 10,000 clones can be screened in one experiment and thus how a new GPC receptor can be cloned using this system.

In this example using the bombesin receptor, two sets of plasmids are utilized. The first contains cDNA coding for the bombesin receptor behind a CMV promoter while the second contains cDNA coding for the marker gene beta-galactosidase is in place of the one for the bombesin receptor. The plasmids are mixed together at different relative concentrations so as to generate 40 µg of total plasmid in each set, but with different quantities of each one. At one extreme, only plasmid coding for bombesin receptor is present. The other mixtures include plasmids for bombesin vs. beta-galactosidase at 1:99, 1:999 and 1:9999.

The different plasmid mixtures are electroporated into separate sets of melanophores which are then plated each in a separate tissue culture plate. Each dish is treated, one at a time with 10 nM melatonin, allowed to incubate for 30 minutes and then either photographed or automatically scanned using a computer controlled imaging system such as one from Scientific Imaging Systems from Knoxville, Tenn.

Next, bombesin is added and after 30 additional minutes, a second photograph is taken as a double exposure over the first one or a second distinct video image is obtained.

In the case of using the photographic procedure the results are like those seen in FIG. 8 wherein cells that respond to the test ligand appear red. In the case of using the video system, the first image is subtracted from the second. A schematic example of this approach is provided by FIG. 14.

Figure 14A:
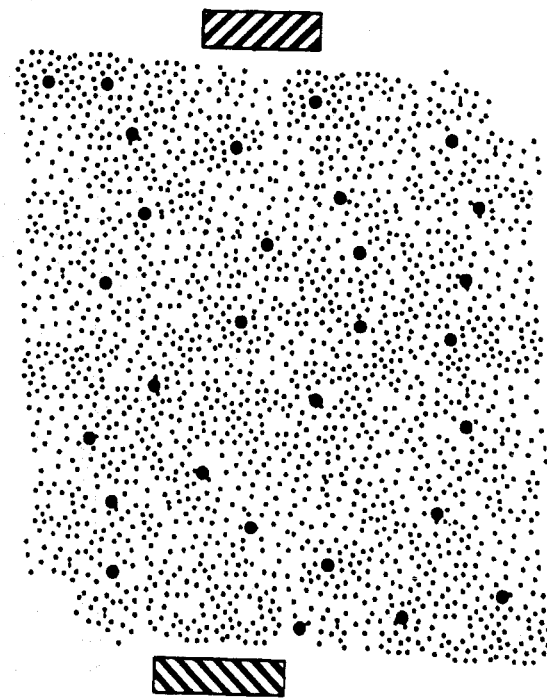
FIG. 14a and 14b are schematic diagrams.

FIG. 14a shows a hypothetical field of cells which have been transfected with a mixture of plasmids containing almost entirely the one for beta-galactosidase and then treated a few days later with melatonin. Small dots represent melanophores with aggregated pigment while large ones represent the background noise created by spurious cells with dispersed melanosomes that have for whatever reason not responded to the melatonin.

Figure 14B:
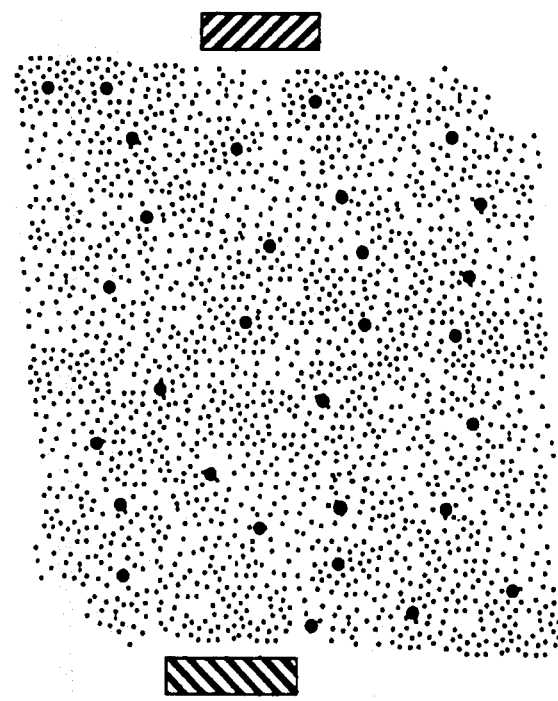

FIG. 14b represents the same field of cells after the addition of bombesin. The image is a negative of the original. The hatched boxes in both FIGS. 14a and 14b serve as aides for aligning the pictures. Analogous markers can be placed on the surface of a real tissue culture plate to allow the computer to match up fields. By aligning the two pictures it is easy to spot the one additional large dot in FIG. 14b by eye or computer. When a bombesin responsive cells is identified, confirmation can be obtained by washing out the added chemicals, repeating the treatments with melatonin and bombesin and determining that either the photographic or video procedure again finds the same cell.

Figure 15:
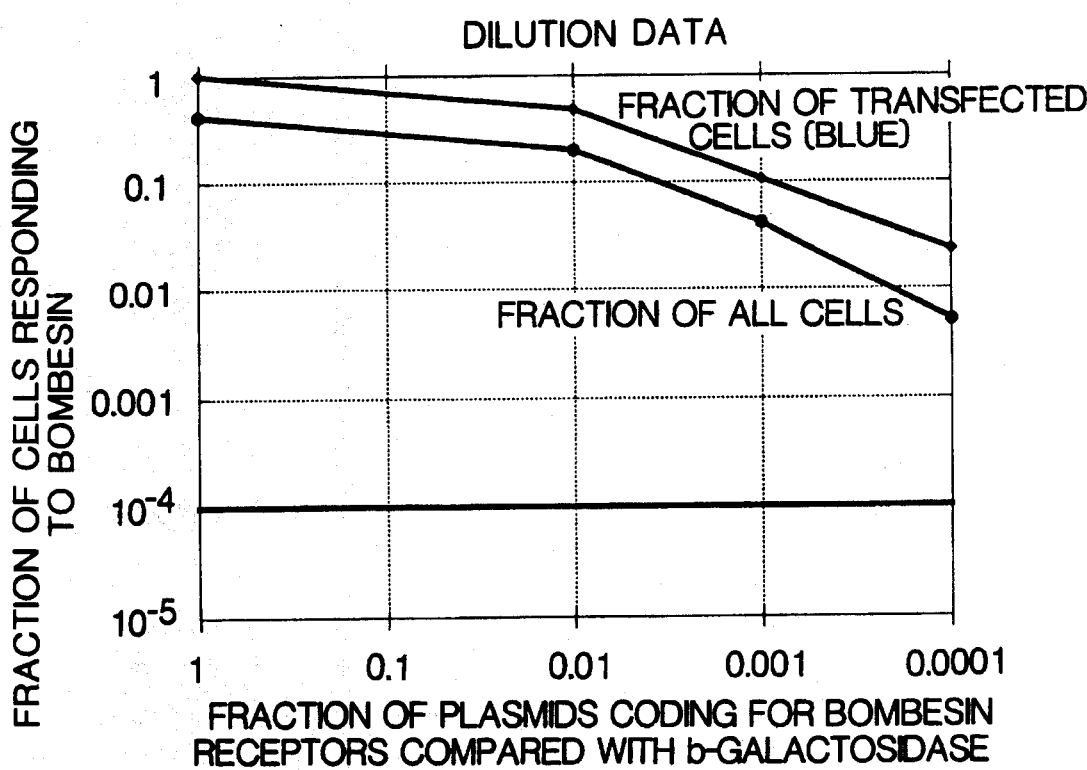
FIG. 15 shows a graph of the fraction of melanophores responding to bombesin following transfection with different combinations of plasmids coding for bombesin receptors vs. beta-galactosidase.

Data from a real set of experiments designed as above are presented in FIG. 15. Three points can be made from the graph. First, and most importantly, it is possible to dilute the plasmid coding for bombesin receptors at least 10,000 fold and still find pigment cells that respond to bombesin. In the particular experiment discussed here the frequency of bombesin receptor cells was 1 in 500 when the bombesin receptor coding plasmid was present at 1 in 10,000. Second, the background noise, i.e., the fraction of cells that will spontaneously disperse their pigment during any given 30 minute experiment is 1 in 10,000 or 20 times below the true signal. Third, the reason that a signal from a plasmid diluted 10,000 fold can be seen over a background noise of 1 cell in 10,000 cells spontaneously dispersing its pigment during the time it takes to run an experiment can be seen from the shape of the curve at high plasmid dilution. It indicates that a cell that expresses foreign DNA is capable of expressing about 100 different plasmids and not just 1. This means that up to 10,000 cDNA clones can be screened in one experimental run when a plasmid coding for a GPC receptor, is being sought.

In order to use the pigment cell assay for cloning GPC receptors some basic considerations are relevant. First, a cDNA library can be constructed in most any standard eukaryotic expression plasmid such as pcDNA1 from Invitrogen. Second, the choice of tissue or cell for making the library can be any that expresses the GPC receptor of interest. Third, one can screen many more than 10,000 clones by simply collecting data from additional sets of cells that have been transfected with different sets of clones from the cDNA library.

To isolate a clone for a GPC receptor, several possible strategies can be employed. One example is a fractionation procedure. When a positive signal is observed, the bacterial colonies that originally gave rise to the pool of 10,000 clones are subdivided into smaller pools, such as 10 sets of 1,000 colonies each. These are expanded, plasmids isolated and each set retested. When a pool gives a positive signal it is subdivided again and the process repeated until a single clone is identified. It has been well documented that a pool screening strategy can be used to clone receptors that couple to G-proteins (Julius, D., MacDermott, A. B., Axel, R. and Jessell, T. M. (1988); "Molecular Characterization of a Functional cDNA encoding the Serotonin 1c Receptor"; *Science* 241: 5458–564).

It will be appreciated that the instant specification is set forth by way of illustration and not limitation, and that various modifications and changes may be made without departing from the spirit and scope of the present invention.

What is claimed is:

1. A method for identifying a chemical that acts as an agonist for a G-protein coupled cell surface receptor (GPC receptor) comprising: introducing to test cells of a pigment cell line capable of dispersing or aggregating their pigment in response to a specific stimulus and expressing an exogenous clone coding for the GPC receptor, a stimulant that sets an initial state of pigment disposition wherein the pigment is aggregated within the test cells if activation of the exogenous GPC receptor induces pigment dispersion, or introducing a stimulant that sets an initial state of pigment disposition wherein the pigment is dispersed within the test cells if activation of the exogenous GPC receptor induces pigment aggregation; contacting the test cells set in an initial state of pigment disposition with the test chemical; and determining whether the pigment disposition in the test cells treated with the chemical is changed from the initial state of pigment disposition, wherein a change in pigment disposition observed in the test cells expressing the exogenous GPC receptor indicates that the chemical is an agonist for the exogenous GPC receptor.

2. The method according to claim 1, wherein the test cells are *Xenopus laevis* melanophores and the stimulant is a chemical or light.

3. The method according to claim 1, wherein the stimulant is melatonin if activation of the exogenous receptor induces pigment dispersion, or light, melanocyte stimulating hormone or a beta 1-adrenergic receptor agonist if activation of the exogenous receptor induces pigment aggregation.

4. The method according to claim 1, further comprising a control operation comprising the steps of: introducing to control cells capable of dispersing or aggregating their pigment in response to a specific stimulus and not expressing the exogenous clone coding for the receptor, a stimulant, that sets an initial state of pigment disposition wherein the pigment is aggregated within the control cells if activation of the exogenous GPC receptor induces pigment dispersion, or introducing a stimulant that sets an initial state of pigment disposition wherein the pigment is dispersed within the control cells if activation of the exogenous GPC receptor induces pigment aggregation; contacting the control cells set in an initial state of pigment disposition with the test chemical; and determining whether the pigment disposition in the control cells treated with the chemical is changed from the initial state of pigment disposition, wherein when no change in pigment disposition is observed in the control cells contacting the chemical, when a change is seen in the test cells it is an indication that the chemical is an agonist for the exogenous GPC receptor.

5. A method for identifying a chemical that acts as an antagonist for a G-protein coupled cell surface receptor (GPC receptor) comprising: introducing to test cells of a pigment cell line capable of dispersing or aggregating their pigment in response to a specific stimulus and expressing an exogenous clone coding for the GPC receptor, a first stimulant that sets an initial state of pigment disposition wherein the pigment is aggregated within the test cells if activation of the exogenous GPC receptor induces pigment dispersion, or introducing a first stimulant that sets an initial state of pigment disposition wherein the pigment is dispersed within the test cells if activation of the exogenous GPC receptor induces pigment aggregation; contacting the test cells set in an initial state of pigment disposition with the chemical to be identified; observing the cells to determine that their state of pigment disposition remains unchanged; adding to the test cells contacted with the chemical to be identified, a second stimulant, that induces pigment dispersion by activating the exogenous GPC receptor if activation of the exogenous GPC receptor induces pigment dispersion, or adding a second stimulant that induces pigment aggregation by activating the exogenous GPC receptor if activation of the exogenous GPC receptor induces pigment aggregation; and determining whether the pigment disposition in the test cells to which the second stimulant was added is changed from the initial state of pigment disposition.

6. The method according to claim 5, wherein the test cells are *Xenopus laevis* melanophores and the stimulant is a chemical or light.

7. The method according to claim 5, wherein the first stimulant is melatonin if activation of the exogenous receptor induces pigment dispersion, or light, melanocyte stimulating hormone or a beta 1-adrenergic receptor agonist if activation of the exogenous receptor induces pigment aggregation.

8. The method according to claim 5, further comprising a control operation comprising the steps of: introducing to control cells of a pigment cell line capable of dispersing or aggregating their pigment in response to a specific stimulus and expressing an exogenous clone coding for the GPC receptor, a first stimulant that sets an initial state of pigment disposition wherein the pigment is aggregated within the control cells if activation of the exogenous GPC receptor induces pigment dispersion, or introducing a first stimulant that sets an initial state of pigment disposition wherein the pigment is dispersed within the test cells if activation of the exogenous GPC receptor induces pigment aggregation; contacting the control cells set in an initial state of pigment disposition with the chemical to be identified; observing the cells to determine that their state of pigment disposition remains unchanged; adding to the control cells contacted with the chemical to be identified, a second stimulant, that induces pigment dispersion by activating an endogenous GPC receptor if activation of the exogenous GPC receptor induces pigment dispersion, or adding a second stimulant that induces pigment aggregation by activating an endogenous GPC receptor if activation of the exogenous GPC receptor induces pigment aggregation; and determining whether the pigment disposition in the control cells to which the second stimulant was added is changed from the initial state of pigment disposition whereby a change in pigment disposition in the control cells, when the test cells show no change, indicates that the first stimulant is an antagonist specific for the exogenous receptor.

9. A method for cloning G-protein coupled cell surface receptors (GPC receptor) comprising introducing to pigment cells derived from a lower animal such as frogs and which are capable of continuous proliferation in vitro, exogenous nucleic acid clones introducing to the cells a stimulant that by activating an endogenous GPC receptor sets an initial state of pigment disposition within the cells; contacting the cells set in an initial state of pigment disposition with a chemical that activates the exogenous receptor; and identifying cells treated with the chemical whose pigment disposition is changed from the initial state of pigment disposition, whereby a change in pigment disposition indicates cells expressing the exogenous clone coding for the receptor.

10. The method according to claim 9, wherein the exogenous nucleic acid clones are from a cDNA library created in a plasmid vector and are introduced to the pigment cells by electroporation.

11. A kit for determining whether a chemical acts as an agonist for an exogenous G-protein coupled cell surface receptor (GPC receptor) comprising in one or more containers: lower animal pigment test cells expressing an exogenous clone coding for the receptor; and a stimulant that induces pigment aggregation by activating an endogenous receptor if activation of the exogenous receptor induces pigment dispersion, and/or a stimulant that induces pigment dispersion by activating an endogenous receptor if activation of the exogenous receptor induces pigment aggregation.

12. The kit according to claim 11, wherein the pigment test cells are *Xenopus laevis* melanophores; the stimulant is melatonin if activation of the exogenous receptor induces pigment dispersion; and the stimulant is a melanocyte stimulating hormone or isoproterenol if activation of the exogenous receptor induces pigment aggregation.

13. A kit for determining whether a chemical acts as an antagonist for an exogenous G-protein coupled cell surface receptor (GPC receptor), comprising in one or more containers: lower animal pigment test cells expressing an exogenous clone coding for the receptor; a first stimulant that induces pigment aggregation by activating an endogenous receptor if activation of the exogenous receptor induces pigment dispersion, and/or a first stimulant that induces pigment dispersion by activating an endogenous receptor if activation of the exogenous receptor induces pigment aggregation; and a second stimulant that induces pigment dispersion by activating the exogenous receptor if activation of the exogenous receptor induces pigment dispersion, and/or a second stimulant that induces pigment aggregation by activating the exogenous receptor if activation of the exogenous receptor induces pigment aggregation.

14. The kit according to claim 13, wherein the pigment test cells are *Xenopus laevis* melanophores; the first stimulant is melatonin, if activation of the exogenous receptor induces pigment dispersion; or the first stimulant is melanocyte stimulating hormone, or isoproterenol if activation of the exogenous receptor induces pigment aggregation.

* * * * *